US008672962B2

(12) United States Patent
Brenneman

(10) Patent No.: US 8,672,962 B2
(45) Date of Patent: Mar. 18, 2014

(54) PERMANENT MAGNET LANCING DEVICE

(75) Inventor: Allen J. Brenneman, Goshen, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 1383 days.

(21) Appl. No.: 11/919,362

(22) PCT Filed: Apr. 26, 2006

(86) PCT No.: PCT/US2006/015704
§ 371 (c)(1),
(2), (4) Date: Oct. 26, 2007

(87) PCT Pub. No.: WO2006/116441
PCT Pub. Date: Nov. 2, 2006

(65) Prior Publication Data
US 2009/0306695 A1    Dec. 10, 2009

Related U.S. Application Data

(60) Provisional application No. 60/675,615, filed on Apr. 28, 2005.

(51) Int. Cl.
*A61B 17/32*    (2006.01)
(52) U.S. Cl.
USPC ........................................................ 606/181
(58) Field of Classification Search
USPC .................... 606/181, 182; 335/207; 600/583
See application file for complete search history.

(56) References Cited

U.S. PATENT DOCUMENTS

| | | | | |
|---|---|---|---|---|
| 2,790,095 | A * | 4/1957 | Peek et al. | 310/103 |
| 3,831,537 | A * | 8/1974 | Siegel | 112/220 |
| 4,207,773 | A * | 6/1980 | Stahovic | 74/25 |
| 6,306,152 | B1 * | 10/2001 | Verdonk et al. | 606/182 |
| 6,517,560 | B1 | 2/2003 | Toth et al. | |
| 7,015,782 | B2 * | 3/2006 | Kincaid et al. | 335/306 |
| 2003/0199909 | A1 | 10/2003 | Boecker et al. | 606/181 |

FOREIGN PATENT DOCUMENTS

EP    1 101 443 A2    5/2001

OTHER PUBLICATIONS

Written Opinion corresponding to International Patent Application Serial No. PCT/2006/015704, European Patent Office, dated Nov. 8, 2006, 6 pages.
International Search Report corresponding to International Patent Application Serial No. PCT/2006/015704, European Patent Office, dated Nov. 8, 2006, 4 pages.

* cited by examiner

*Primary Examiner* — Ryan Severson
*Assistant Examiner* — Sarah Simpson
(74) *Attorney, Agent, or Firm* — Nixon Peabody LLP

(57) ABSTRACT

A lancing device and a method for using the lancing device includes a plunger mechanism having a permanent magnet housed therein. The lancing device includes a movable element having at least one attracting object and at least one repelling object. The attracting object attracts the permanent magnet to move the plunger into a retracted position. The repelling object repels the permanent magnet to move the plunger into a lancing position to pierce the skin of a test subject. The use of the permanent magnet in the plunger mechanism reduces or eliminates multiple punctures due to plunger bounce or oscillation that can occur while a body fluid sample is being drawn.

17 Claims, 7 Drawing Sheets

PERMANENT MAGNET LANCING DEVICE

CROSS-REFERENCE TO RELATED APPLICATIONS

This application claims priority to Application No. 60/675,615 filed on Apr. 28, 2005, which is incorporated by reference in its entirety.

FIELD OF THE INVENTION

The present invention relates generally to lancing devices and methods of using the same, and more particularly, to lancing devices for drawing a body fluid sample and methods of using the same that reduce or eliminate multiple punctures due to plunger bounce or oscillation.

BACKGROUND OF THE INVENTION

The quantitative determination of analytes in body fluids is of great importance in the diagnoses and maintenance of certain physiological abnormalities. For example, lactate, cholesterol, bilirubin and glucose should be monitored in certain individuals. In particular, monitoring glucose levels is important to diabetic individuals who must frequently check the glucose level in their body fluids to regulate the glucose intake in their diets. To monitor glucose levels, a whole blood sample may be used.

One method of obtaining a body fluid sample, such as a whole blood sample, is to use a lancing device. Existing lancing devices use a lancet to pierce the tissue of the skin, allowing a whole blood sample to form on the skin's surface. The whole blood sample is then transferred to the testing device. The whole blood sample is often taken from the fingertips of a test subject for glucose monitoring because of the high concentration of capillaries that can provide an effective blood supply. Taking the blood from the fingertips, however, is disadvantageous because of the high concentration of nerve endings that cause pain and discomfort to many individuals.

In addition to the pain and discomfort inherent in piercing the fingertip, existing lancing devices that use coil springs to produce the lancing force may cause increased pain to individuals due to the oscillatory nature of the springs. Coil springs by their nature have a natural frequency vibration and continue to oscillate after being displaced from their natural length and released. This oscillation continues until internal or external damping causes the oscillation to cease. This continued oscillation may result in multiple punctures to the individual's skin, thereby increasing the discomfort to the user. Furthermore, lancing devices with coil springs, or any other mechanical springs, make automated and manual assembly difficult because the coil springs may nest together, can be damaged in handling, and require more assembly time.

It would be desirable to have a lancing device and a method for using a lancing device that addresses these issues.

SUMMARY OF THE INVENTION

A lancing device is disclosed according to one embodiment of the present invention. The lancing device includes a plunger, a lancet, and a movable element. The plunger has a first end and a second end. The first end of the plunger has a permanent magnet. The lancet is removably connected to the second end of the plunger and is adapted to pierce the skin of a test subject. The movable element is adjacent to the first end of the plunger. The movable element includes an attracting object and a repelling object. The attracting object comes in close proximity to the permanent magnet so as to attract the permanent magnet and move the plunger into a retracted position. The repelling object comes in close proximity to the permanent magnet to repel the permanent magnet and move the plunger into a lancing position.

A method for using a lancing device is disclosed according to one embodiment of the present invention. The method includes the act of providing a lancing device that includes a plunger having a first end and a second end, a lancet removably connected to the second end of the plunger and adapted to pierce the skin of a test subject, and a movable element adjacent to the first end of the plunger. The movable element is comprised of an attracting object and a repelling object. The first end of the plunger has a permanent magnet. The method includes the act of retracting the plunger by positioning the movable element such that the attracting object generally aligns with and attracts the permanent magnet. The method further includes the act of moving the plunger and lancet forward to pierce the skin of a user by positioning the movable element such that the repelling object generally aligns with and repels the permanent magnet.

A lancing device is disclosed according to another embodiment of the present invention. The lancing device includes a plunger, a lancet and a rotary element. The plunger has a first end and a second end. The first end of the plunger has a permanent magnet. The lancet is removably connected to the second end of the plunger and adapted to pierce the skin of a test subject. The rotary element is adjacent to the first end of the plunger. The rotary element includes a first magnet, a second magnet and an attracting object. The rotary element is adapted to move in a circular motion from a first position in which the first magnet attracts the permanent magnet to a second position in which the second magnet repels the permanent magnet to a third position in which the attracting object attracts the permanent magnet. The first position is adapted to cause the plunger and lancet to retract. The second position is adapted to cause the plunger to move forward and pierce the skin of a user via the lancet. The third position is adapted to cause the plunger to withdraw the lancet from the skin of the user.

A lancing device is disclosed according to further embodiment of the present invention. The lancing device includes a plunger, a lancet and a linear element. The plunger has a first end and a second end. The first end of the plunger has a permanent magnet. The lancet is removably connected to the second end of the plunger and adapted to pierce the skin of a test subject. The linear element is adjacent to the first end of the plunger. The linear element includes a first magnet, a second magnet and an attracting object. The linear element is adapted to move along an axis perpendicular to the plane of the plunger from a first position in which the first magnet attracts the permanent magnet to a second position in which the second magnet repels the permanent magnet to a third position in which the attracting object attracts the permanent magnet. The first position is adapted to cause the plunger and lancet to retract. The second position is adapted to cause the plunger to move forward and pierce the skin of a user via the lancet. The third position is adapted to cause the plunger to withdraw the lancet from the skin of the user.

The above summary of the present invention is not intended to represent each embodiment, or every aspect, of the present invention. Additional features and benefits of the present invention are apparent from the detailed description, and figures set forth below.

BRIEF DESCRIPTION OF THE DRAWINGS

FIG. 1b is an enlarged view of the plunger mechanism of the lancing device of FIG. 1a.

DESCRIPTION OF ILLUSTRATED EMBODIMENTS

The present invention is directed to a lancing device that is adapted to receive a lancet for use in drawing a body fluid sample from a test subject. The body fluid sample generally contains at least one analyte. The body fluid sample may be analyzed with a meter and test strip, or similar device, to determine the concentration of the analyte to be examined. Examples of the types of analytes which may be collected with a lancing device include glucose, lipid profiles (e.g., cholesterol, triglycerides, LDL and HDL), microalbumin, hemoglobin $A_{1C}$, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids. As used within this application, the term "concentration" refers to an analyte concentration, activity (e.g., enzymes and electrolytes), titers (e.g., antibodies), or any other measure concentration used to measure the desired analyte.

Figure 1A:
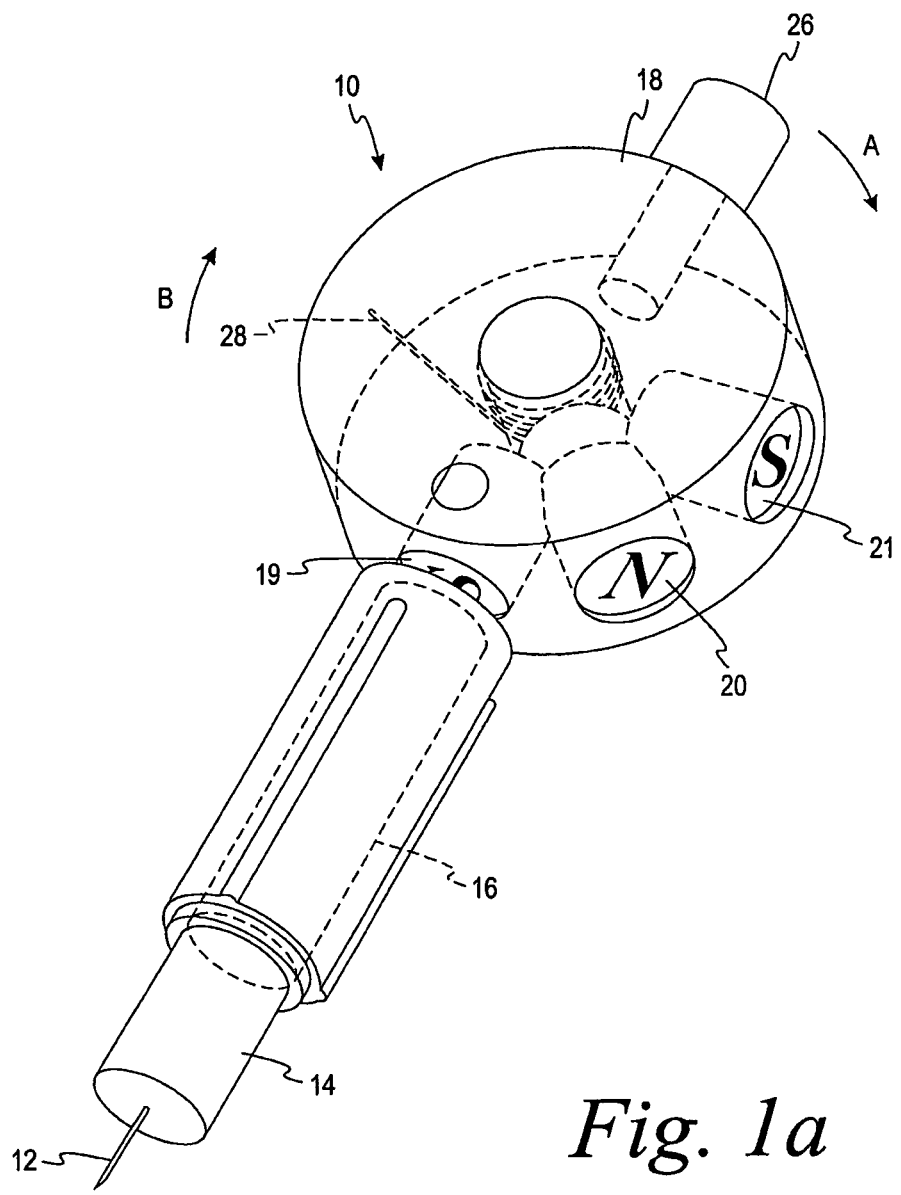
FIG. 1a is a perspective view of a lancing device having a rotating disc positioned to move a plunger mechanism into a retracted position, according to one embodiment of the present invention.
Figure 6:
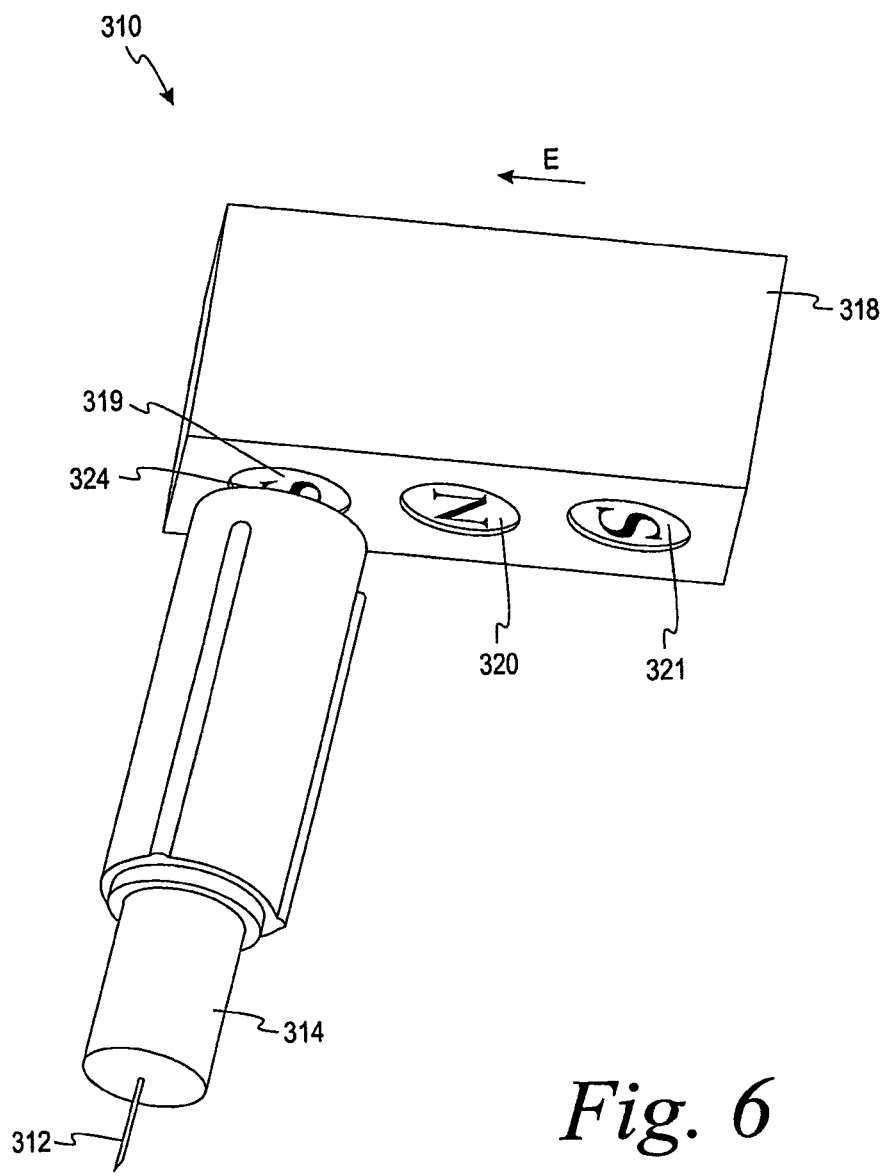
FIG. 6 is perspective view of a lancing device having a linear slide, according to a further embodiment of the present invention.

Turning now to the drawings and initially to FIG. 1a, a lancing device 10 is shown according to one embodiment of the present invention. The lancing device 10 includes a lancet 12, a lancet holder 14, a plunger mechanism 16 and a movable element 18. The movable element 18 may include a rotating disc or component, as shown in FIG. 1a, a linear slide or component, as shown in FIG. 6, or any other device that is adapted to move between a plurality of positions, i.e., from a first position to a second position. The movable element 18 also includes at least one attracting object 19 and one repelling object 20. As shown in the embodiment in FIG. 1a, the movable element 18 may also include a second attracting object 21. Also included in the lancing device 10 in FIG. 1a are an actuator button 26 and a torsion spring 28.

Figure 1B:
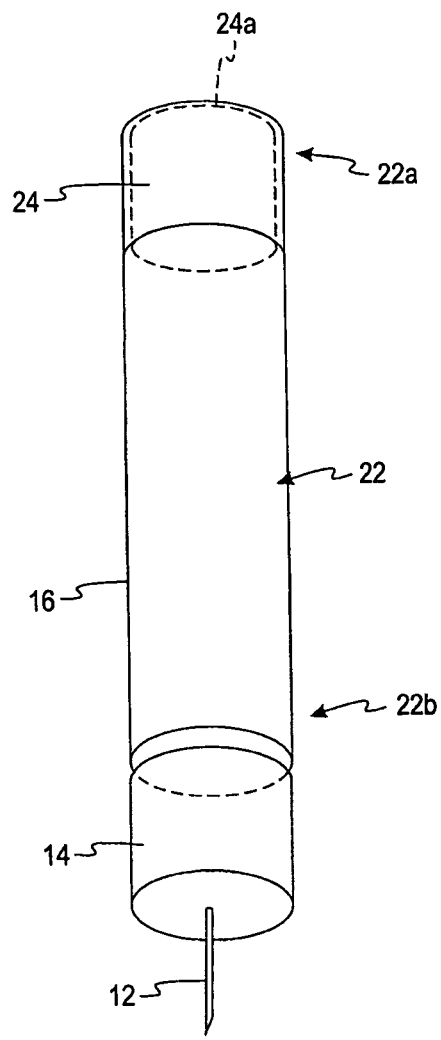

The plunger mechanism 16 is shown in more detail in FIG. 1b. In FIG. 1b, the plunger mechanism 16 includes a plunger 22 that has a first end 22a and a second end 22b. The first end 22a of the plunger 22 is adjacent to the movable element 18. The second end 22b of the plunger 22 is removably attached to the lancet 12 via the lancet holder 14. The first end 22a of the plunger 22 is adapted to include a permanent magnet 24 that is at least partially enclosed within the plunger 22 according to one embodiment. A portion 24a of the permanent magnet 24 comes in close proximity to the movable element 18. The portion 24a of the permanent magnet 24 may include either the north or south magnetic pole of the permanent magnet 24.

In one embodiment of the present invention, as shown in FIG. 1a, the attracting object 19, the repelling object 20, and the second attracting object 21 are magnets having north ("N") and south ("S") magnetic poles. As the movable element 18 is moved, i.e. rotated or slid, the portion 24a of the permanent magnet 24 comes in close proximity to these north and south magnetic poles. Attractive and repulsive forces occur between the permanent magnet 24 and the north and south magnetic poles of the attracting object 19, the repelling object 20, and the second attracting object 21, causing the plunger 22 containing the permanent magnet 24 to move into retracted, lancing and retracted positions, respectively. In additional to magnets, the attracting objects may be comprised of any ferrous metal, including but not limited to, iron, steel or a combination thereof.

Figure 2:
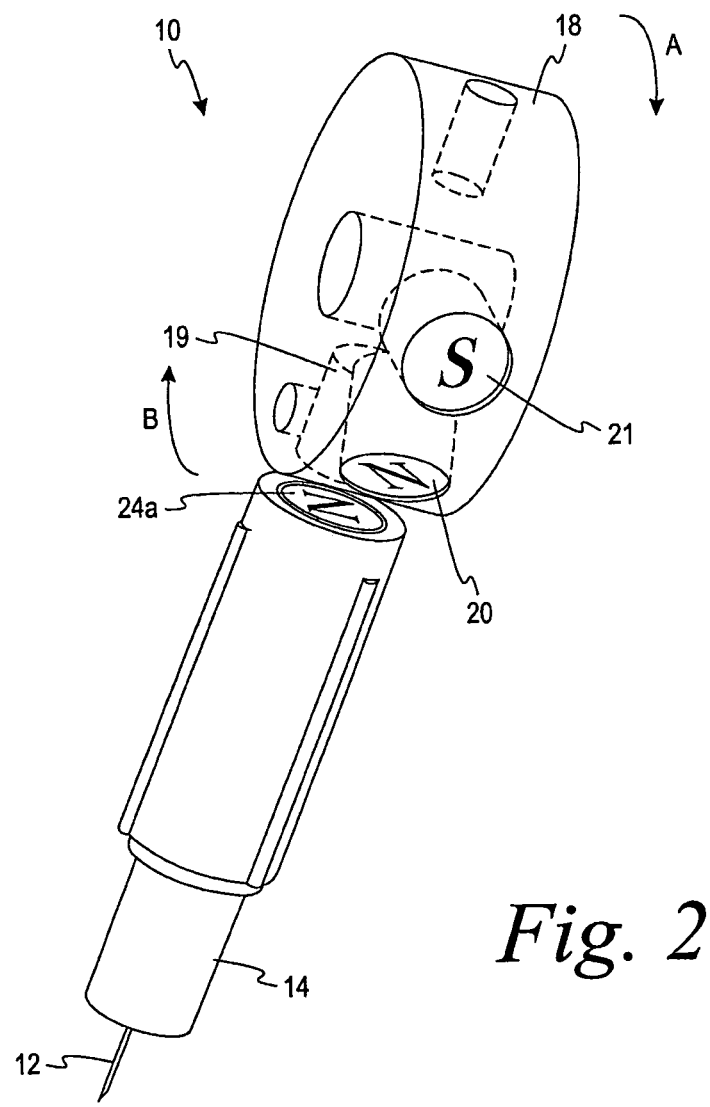
FIG. 2 is a perspective view of the lancing device of FIG. 1a having a rotating disc positioned to move the plunger mechanism into a lancing position, according to one embodiment of the present invention.

FIGS. 1a and 2 may be used to show the method of using the lancing device 10 in more detail. The movable element 18 may be manually moved by a user by rotating the movable element 18 in a circular motion using the actuator button 26. Alternatively, the movable element 18 may be spring-loaded so that a user can merely release the movable element to cause the spring to initiate the rotation or the linear motion. FIG. 1a shows one example of the movable element 18 having a torsion spring 28. The torsion spring 28 may be installed so that it is preloaded when the attracting object 19 is in line with the plunger 22. This means that the torsion spring 28 is installed without being in a neutral condition. The torsion spring 28 is wrapped up so that when the attracting object 19 is generally aligned with the permanent magnet 24, the spring is already applying a torsion force to the movable element 18. When the torsion spring 28 is released, it will rotate the movable element in a clockwise direction.

When the user releases the actuator button 26, the torsion spring 28 rotates the movable element 18 in a clockwise direction such that the repelling object 20 is generally aligned with the permanent magnet 24, causing the plunger 22 to move into a lancing position to pierce the skin of the user. The torsion spring 28 continues to rotate the movable element such that the second attracting object 21 is generally aligned with the permanent magnet 24 to withdraw the lancet 12 from the skin of the user. At this stage, the torsion spring 28 is no longer preloaded.

As described generally above, a user of the lancing device 10 rotates the movable element 18 in a circular motion (in the direction of arrows A and B of FIG. 1a) into various positions, the movable element 18 being configured to switch from attracting the permanent magnet 24 to repelling the permanent magnet 24 with an angular rotation of the movable element 18 of no more than 90 degrees. As the movable element 18 of FIG. 1a is rotated such that the south pole of the attracting object 19 is generally aligned with and in close proximity to the north pole of the permanent magnet 24a, the differing polarities cause the permanent magnet 24 to be attracted to the attracting object 19. The attractive forces cause the plunger 22 containing the permanent magnet 24 to move toward the attracting object 19 in a direction generally perpendicular to the plane of the permanent magnet 24. This movement of the plunger 22 toward the attracting object 19 places the plunger 22 in a retracted position. The retracted position indicates that the plunger 22, lancet holder 14 and lancet 12 are ready to be used to pierce the skin of a test subject and draw a body fluid sample.

Referring now to FIG. 2, from a retracted position, the movable element 18 may be rotated such that the permanent magnet 24 is moved away from the attracting object 19 and closer to the repelling object 20. Once the north pole of the permanent magnet 24a becomes generally aligned with and in close proximity to the north pole of the repelling object 20, the repulsive forces will cause the plunger 22 containing the permanent magnet 24 to move away from the repelling object 20. This movement away from the repelling object 20 causes the lancet 12 to move into a lancing position for piercing the skin of the test subject.

Once the lancet 12 pierces the skin of the test subject and a body fluid sample is produced, the lancet 12 is withdrawn from the skin of the test subject by rotating the movable element 18 such that the permanent magnet 24 is generally aligned with and in close proximity to the second attracting object 21. The attractive forces between the south pole of the second attracting object 21 and the north pole of the permanent magnet 24a cause the plunger 22 to move back towards the second attracting object 21 and withdraw the lancet 12 from the test subject's skin, thus returning the plunger 22 to a retracted position.

Figure 3:
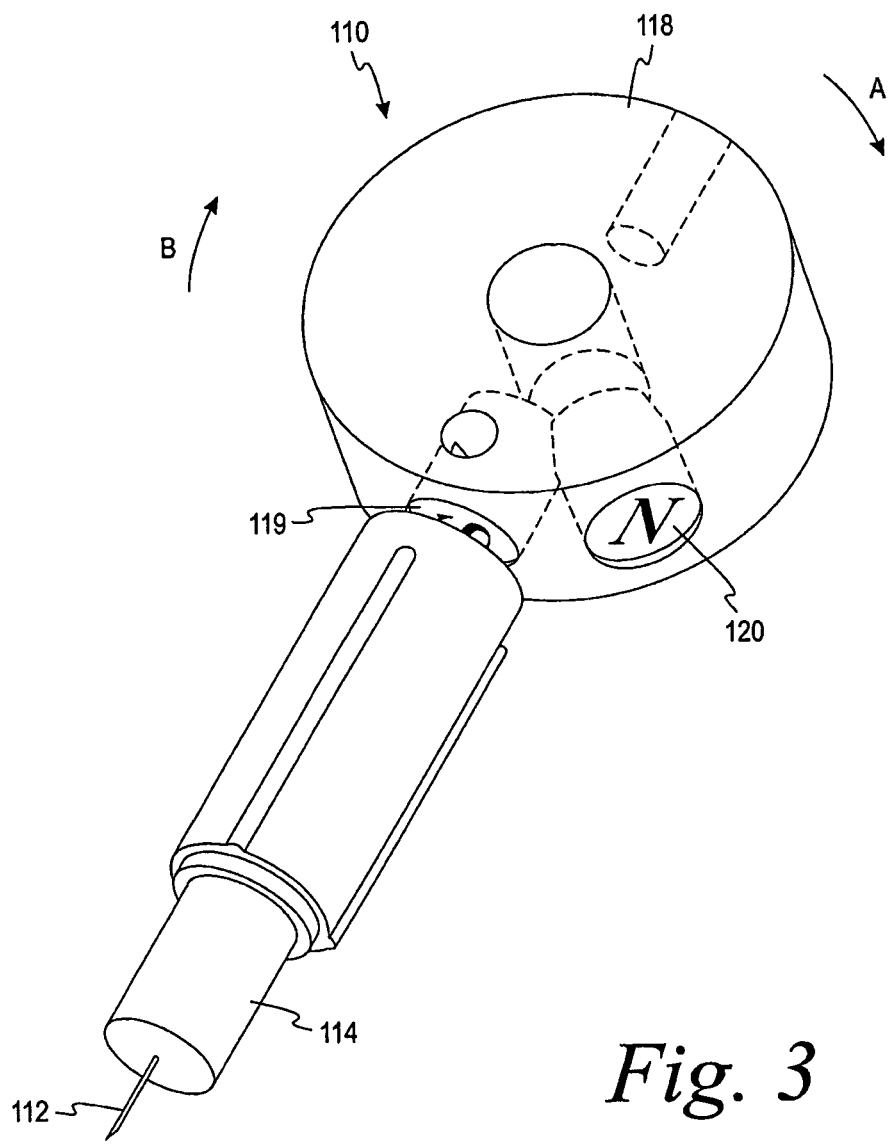
FIG. 3 is a perspective view of a lancing device according to another embodiment of the present invention.

In other embodiments contemplated by the present invention, as shown in FIG. 3, the movable element 118 may include only a single attracting object 119. Thus, to withdraw the lancet 112 from the skin of a test subject and move the plunger (not shown) from a lancing position to a retracted position, it is contemplated that the movable element 118 may be moved such that the permanent magnet (not shown) is aligned again with the first attracting object 119 instead of with a second attracting object 21 as described above. Furthermore, in addition to including a magnet as an attracting object 119, other objects may be used to attract the permanent magnet and move the plunger into a retracted position, such as metal clips, metal inserts, etc. These metal clips or inserts may be comprised of any ferrous metal, including but not limited to iron, steel or a combination thereof.

Figure 4:
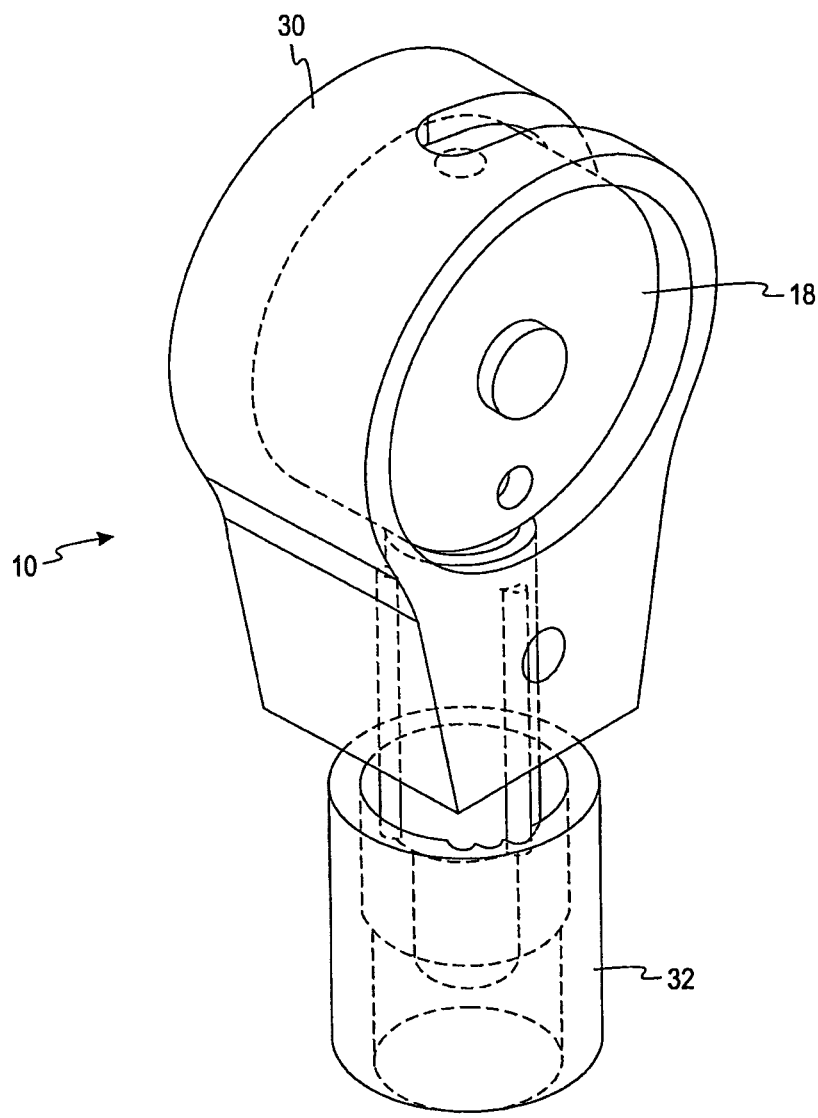
FIG. 4 is a perspective view of the lancing device of FIG. 1a, with a housing and endcap.

Turning now to FIG. 4, the lancing device 10 of the present invention is shown having a housing 30 that encloses at least a portion of the movable element 18. The housing protects the elements of the lancing device 10. A removable endcap 32 is attached to one end of the lancing device 10. The endcap 32 surrounds at least a portion of the lancet 12 and lancet holder 14. The endcap serves to set the depth of puncture and to protect the user from inadvertently piercing the test subject's skin with the lancet 12.

Figure 5:
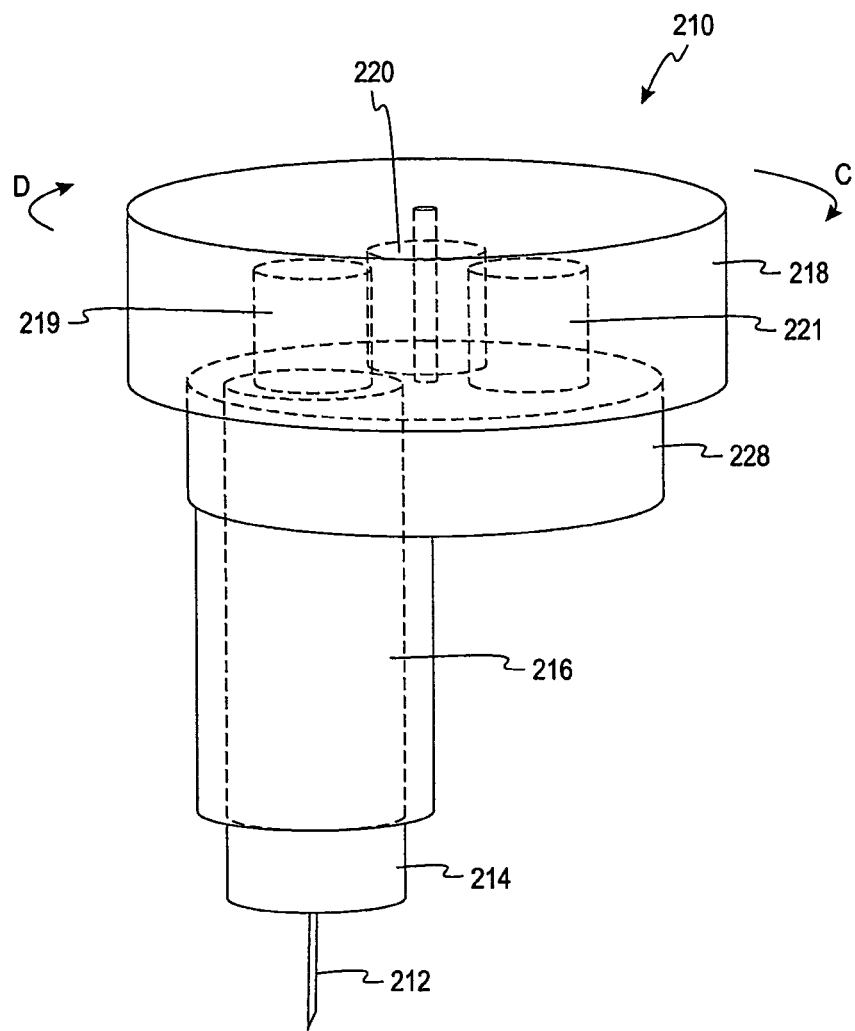
FIG. 5 is a perspective view of a lancing device according to a further embodiment of the present of the present invention.

As shown in FIGS. 1a, 2 and 3, the movable element 18 may be positioned such that the axis of rotation is perpendicular to the plunger and lancet axis. Alternatively, as shown in the embodiment in FIG. 5, the movable element 218 may be positioned such that the axis of rotation is aligned with the plunger and lancet axis. In this embodiment, the movable element 218 may be rotated in the direction as illustrated by arrows C and D. Attracting objects 219, 221 and repelling object 220 are generally aligned with and in close proximity to the permanent magnet located at one end of the plunger mechanism 216. As described above, the lancet holder 214 and the lancet 212 may be brought into retracted and lancing positions as the movable element 218 is rotated. FIG. 5 also illustrates a portion of the housing 228 that protects certain elements of the lancing device 220.

Turning now to FIG. 6, another alternative embodiment of the present invention is shown having a linear slide or element 318 as the movable element. The linear slide 318 of the lancing device 310 in FIG. 6 is adapted to move the plunger into retracted and lancing positions. Similar to the rotating disc of FIG. 1a, the linear slide 318 includes attracting objects 319, 321 and a repelling object 320 that are magnets. The attracting object 319 when aligned with the permanent magnet 324 attracts the permanent magnet 324 such that the plunger (not shown) and lancet 312 are moved into a retracted position. To move the plunger and lancet 312 into a lancing position, the linear slide 318 is moved in a linear motion in a direction perpendicular to the axis of the plunger (in the direction of arrow E in FIG. 6) to bring the repelling object 320 into general alignment with the permanent magnet 324. Once the lancet 312 pierces the skin of a test subject to provide a body fluid sample, the linear slide 318 is moved, i.e., slid, such that the attracting object 321 is in general alignment with the permanent magnet 324 and the lancet 312 is withdrawn from the skin.

In addition to a magnet, the attracting object 319 of the alternative embodiment of FIG. 6 may also include a metal clip, a metal insert, etc. These metal clips or inserts may be comprised of any ferrous metal, including but not limited to iron, steel or a combination thereof.

Like lancing devices that use coil springs, this method of moving the movable element from a retracted position to a lancing position and back to a retracted position must occur within only milliseconds after the lancing device is positioned on the test subject's skin and activated. However, even within this short time frame, current lancing devices that use coil springs introduce multiple punctures as the coil springs continue to oscillate. The present invention reduces or eliminates the introduction of multiple punctures by using magnets or other attracting and repelling objects to provide the lancing and retracting forces.

Alternative Embodiment A

A lancing device comprising:
a plunger having a first end and a second end, the first end of the plunger having a permanent magnet;
a lancet removably connected to the second end of the plunger and adapted to pierce the skin of a test subject; and
a movable element adjacent to the first end of the plunger, the movable element including an attracting object and a repelling object, the attracting object coming in close proximity to the permanent magnet so as to attract the permanent magnet and move the plunger into a retracted position, the repelling object coming in close proximity to the permanent magnet to repel the permanent magnet and move the plunger into a lancing position.

Alternative Embodiment B

The lancing device according to Alternative Embodiment A further comprising a housing that encloses at least a portion of the movable element.

Alternative Embodiment C

The lancing device according to Alternative Embodiment A wherein the movable element is a rotating disc.

Alternative Embodiment D

The lancing device according to Alternative Embodiment A wherein the movable element is a linear slide.

Alternative Embodiment E

The lancing device according to Alternative Embodiment A wherein the attracting object is a magnet having a different polarity than the permanent magnet.

Alternative Embodiment F

The lancing device according to Alternative Embodiment A wherein the attracting object is a metal insert having a different polarity than the permanent magnet.

Alternative Embodiment G

The lancing device according to Alternative Embodiment F wherein the metal insert comprises ferrous material including iron, steel or a combination thereof.

Alternative Embodiment H

The lancing device according to Alternative Embodiment A wherein the repelling object is a magnet having a similar polarity as the permanent magnet.

Alternative Embodiment I

The lancing device according to Alternative Embodiment A wherein the movable element includes a plurality of attracting objects.

Alternative Embodiment J

The lancing device according to Alternative Embodiment A wherein the movable element includes a plurality of repelling objects.

Alternative Process K

A method for using a lancing device, the method comprising the acts of: providing a lancing device including,
a plunger having a first end and a second end, the first end of the plunger having a permanent magnet,
a lancet removably connected to the second end of the plunger and adapted to pierce the skin of a test subject, and
a movable element adjacent to the first end of the plunger, the movable element comprising an attracting object and a repelling object;
retracting the plunger by positioning the movable element such that the attracting object generally aligns with and attracts the permanent magnet; and
moving the plunger and lancet forward to pierce the skin of a user by positioning the movable element such that the repelling object generally aligns with and repels the permanent magnet.

Alternative Process L

The method according to Alternative Process K further comprising withdrawing the plunger and lancet by positioning the movable element such that the attracting object generally aligns with and attracts the permanent magnet.

Alternative Process M

The method according to Alternative Process K further comprising withdrawing the plunger and lancet by positioning the movable element such that a second attracting object generally aligns with and attracts the permanent magnet.

Alternative Process N

The method according to Alternative Process K wherein the movable element is a rotating disc.

Alternative Process O

The method according to Alternative Process K wherein the movable element is a linear slide.

Alternative Process P

The method according to Alternative Process K wherein the attracting object is a magnet having a different polarity than the permanent magnet.

Alternative Process Q

The method according to Alternative Process K wherein the second attracting object is a metal insert having a different polarity than the permanent magnet.

Alternative Process R

The method according to Alternative Process Q wherein the metal insert comprises ferrous material including iron, steel or a combination thereof.

Alternative Process S

The method according to Alternative Process K wherein the repelling object is a magnet having a similar polarity as the permanent magnet.

Alternative Process T

The method according to Alternative Process K wherein the movable element includes a plurality of attracting objects.

Alternative Process U

The method according to Alternative Process K wherein the movable element includes a plurality of repelling objects.

Alternative Embodiment V

A lancing device comprising:
a plunger having a first end and a second end, the first end of the plunger having a permanent magnet;
a lancet removably connected to the second end of the plunger and adapted to pierce the skin of a test subject; and
a rotary element adjacent to the first end of the plunger, the rotary element including a first magnet, a second magnet and an attracting object, the rotary element is adapted to move in a circular motion from a first position in which the first magnet attracts the permanent magnet to a second position in which the second magnet repels the permanent magnet to a third position in which the attracting object attracts the permanent magnet, the first position is adapted to cause the plunger and lancet to retract, the second position is adapted to cause the plunger to move forward and pierce the skin of a user via the lancet, and the third position is adapted to cause the plunger to withdraw the lancet from the skin of the user.

Alternative Embodiment W

The lancing device of Alternative Embodiment V wherein the attracting object is a third magnet.

Alternative Embodiment X

The lancing device of Alternative Embodiment V wherein the attracting object is a metal insert.

Alternative Embodiment Y

The lancing device of Alternative Embodiment X wherein the metal insert comprises ferrous material including iron, steel or a combination thereof.

Alternative Embodiment Z

The lancing device of Alternative Embodiment V wherein the rotary element is adapted to return to the first position from the second position such that the first magnet attracts the permanent magnet and causes the plunger to withdraw the lancet from the skin of the user.

Alternative Embodiment AA

A lancing device comprising:
a plunger having a first end and a second end, the first end of the plunger having a permanent magnet;
a lancet removably connected to the second end of the plunger and adapted to pierce the skin of a test subject; and
a linear element adjacent to the first end of the plunger, the linear element including a first magnet, a second magnet and an attracting object, the linear element is adapted to move along an axis perpendicular to the plane of the plunger from a first position in which the first magnet attracts the permanent magnet to a second position in which the second magnet repels the permanent magnet to a third position in which the attracting object attracts the permanent magnet, the first position is adapted to cause the plunger and lancet to retract, the second position is adapted to cause the plunger to move forward and pierce the skin of a user via the lancet, and the third position is adapted to cause the plunger to withdraw the lancet from the skin of the user.

Alternative Embodiment BB

The lancing device of Alternative Embodiment AA wherein the attracting object is a third magnet.

Alternative Embodiment CC

The lancing device of Alternative Embodiment AA wherein the attracting object is a metal insert.

Alternative Embodiment DD

The lancing device of Alternative Embodiment CC wherein the metal insert comprises ferrous material including iron, steel or a combination thereof.

Alternative Process EE

A method for using a lancing device, the lancing device including a plunger having a permanent magnet and a rotating component adjacent to the plunger, the rotating component having at least one attracting object and at least one repelling object, the method comprising the acts of:
moving the plunger into a retracted position by turning the rotating component until the attracting object attracts the permanent magnet;
moving the plunger into a lancing position by turning the rotating component until the repelling object repels the permanent magnet; and
lancing the skin of a user while the plunger is in the lancing position.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A lancing device comprising:
a plunger having a first end and a second end, the first end of the plunger having a permanent magnet;
a lancet removably connected to the second end of the plunger and adapted to pierce the skin of a test subject;
a movable element adjacent to the first end of the plunger, the movable element including an attracting object and a repelling object, the attracting object being configured to come in close proximity to the permanent magnet so as to attract the permanent magnet and to cause the plunger to move into a retracted position, the repelling object being configured to come in close proximity to the permanent magnet to repel the permanent magnet and to cause the plunger to move into a lancing position, the movable element being configured to switch from attracting the permanent magnet to repelling the permanent magnet with an angular rotation of the movable element of no more than 90 degrees; and
a biasing member configured to cause the movable element to rotate,
wherein the movable element includes no more than three attracting objects and repelling objects in total that assist in causing the plunger to move between the retracted position and the lancing position.

2. The lancing device according to claim 1, further comprising a housing that encloses at least a portion of the movable element.

3. The lancing device according to claim 1, wherein the movable element is a rotating disc.

4. The lancing device according to claim 1, wherein the attracting object is a magnet having a different polarity than the permanent magnet.

5. The lancing device according to claim 1, wherein the attracting object is a metal insert having a different polarity than the permanent magnet.

6. The lancing device according to claim 1, wherein the repelling object is a magnet having a similar polarity as the permanent magnet.

7. The lancing device according to claim 1, wherein the movable element includes a second attracting object.

8. The lancing device according to claim 1, wherein the movable element includes a second repelling object.

9. The lancing device of claim 1, wherein the biasing member is a torsion spring.

10. The lancing device of claim 1, wherein the biasing member is configured to cause the movable element to rotate from a first position in which the movable element is configured to attract the permanent magnet to a second position in which the movable element is configured to repel the permanent magnet.

11. The lancing device of claim 10, wherein the biasing member is further configured to cause the movable element to rotate from the second position to a third position in which the movable element is configured to attract the permanent magnet.

12. The lancing device of claim 1, further comprising an actuator configured to be activated to permit the biasing member to rotate the movable element.

13. A lancing device comprising:
a plunger having a first end and a second end, the first end of the plunger having a permanent magnet;
a lancet removably connected to the second end of the plunger and adapted to pierce the skin of a test subject;
a rotary element adjacent to the first end of the plunger, the rotary element including a first magnet, a second magnet and an attracting object, the rotary element is adapted to move in a circular motion from a first position in which the first magnet attracts the permanent magnet to a second position in which the second magnet repels the permanent magnet to a third position in which the attracting object attracts the permanent magnet, the first position is adapted to cause the plunger and lancet to retract, the second position is adapted to cause the plunger to move forward and pierce the skin of a user via the lancet, and the third position is adapted to cause the plunger to withdraw the lancet from the skin of the user, the rotary element being configured to switch from attracting the permanent magnet in the first position to repelling the permanent magnet in the second position with an angular rotation of the movable element of no more than 90 degrees; and
a biasing member configured to cause the rotary element to rotate,
wherein the rotary element includes no more than three magnets and attracting objects in total that assist in moving the plunger between the first position, the second position, and the third position.

14. The lancing device of claim 13, wherein the attracting object is a third magnet.

15. The lancing device of claim 13, wherein the attracting object is a metal insert.

16. The lancing device of claim 13, wherein the biasing member is a torsion spring.

17. The lancing device of claim 13, further comprising an actuator configured to be activated to permit the biasing member to rotate the rotary element.

* * * * *

UNITED STATES PATENT AND TRADEMARK OFFICE
CERTIFICATE OF CORRECTION

| | | |
|---|---|---|
| PATENT NO. | : 8,672,962 B2 | Page 1 of 1 |
| APPLICATION NO. | : 11/919362 | |
| DATED | : March 18, 2014 | |
| INVENTOR(S) | : Brenneman | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1500 days.

Signed and Sealed this
Eleventh Day of August, 2015

Michelle K. Lee
*Director of the United States Patent and Trademark Office*